US009694116B2

(12) United States Patent
Wu

(10) Patent No.: US 9,694,116 B2
(45) Date of Patent: Jul. 4, 2017

(54) STENTS WITH RADIOPAQUE MARKERS

(71) Applicant: Abbott Cardiovascular Systems Inc., Santa Clara, CA (US)

(72) Inventor: Patrick P. Wu, San Carlos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 15/151,365

(22) Filed: May 10, 2016

(65) Prior Publication Data

US 2016/0250396 A1 Sep. 1, 2016

Related U.S. Application Data

(63) Continuation of application No. 14/693,679, filed on Apr. 22, 2015, now Pat. No. 9,358,325, which is a (Continued)

(51) Int. Cl.
*A61F 2/958* (2013.01)
*A61L 31/18* (2006.01)
(Continued)

(52) U.S. Cl.
CPC ............... *A61L 31/18* (2013.01); *A61F 2/06* (2013.01); *A61F 2/82* (2013.01); *A61F 2/844* (2013.01); *A61F 2/90* (2013.01); *A61F 2/915* (2013.01); *A61F 2/95* (2013.01); *A61F 2/958* (2013.01); *A61L 29/00* (2013.01); *A61L 31/04* (2013.01); *A61L 31/06* (2013.01); *A61L 31/148* (2013.01); *B29C 65/48* (2013.01); *B29D 23/00* (2013.01); *A61B 2090/3966* (2016.02); *A61F 2002/91516* (2013.01); *A61F 2002/91566* (2013.01); *A61F 2002/91583* (2013.01); *A61F 2002/9522* (2013.01); *A61F 2230/0013* (2013.01); *A61F 2230/0054* (2013.01); *A61F 2250/0098* (2013.01); *B29L 2031/7543* (2013.01); *Y10T 29/49885* (2015.01); *Y10T 29/49913* (2015.01); *Y10T 29/49927* (2015.01);
(Continued)

(58) Field of Classification Search
CPC .. B21D 39/048; A61F 2250/0098; A61F 2/82; Y10T 29/49927; Y10T 29/49993
See application file for complete search history.

(56) References Cited

U.S. PATENT DOCUMENTS 2,697,863 A 12/1954 Moser
3,476,463 A 11/1969 Kreuzer
(Continued)

FOREIGN PATENT DOCUMENTS

CN 1241442 1/2000
DE 44 07 079 9/1994
(Continued)

OTHER PUBLICATIONS

U.S. Appl. No. 11/009,977, Pacetti, filed Dec. 9, 2004.
(Continued)

*Primary Examiner* — Jermie Cozart
(74) *Attorney, Agent, or Firm* — Squire Patton Boggs (US) LLP

(57) ABSTRACT

Various embodiments of stents with radiopaque markers arranged in patterns are described herein.

2 Claims, 8 Drawing Sheets

A — A
220
225
225
230
235

Related U.S. Application Data continuation of application No. 14/273,127, filed on May 8, 2014, now Pat. No. 9,038,260, which is a continuation of application No. 13/964,008, filed on Aug. 9, 2013, now Pat. No. 8,752,268, which is a continuation of application No. 11/796,226, filed on Apr. 26, 2007, now abandoned, said application No. 14/273,127 is a continuation of application No. 13/964,006, filed on Aug. 9, 2013, now Pat. No. 8,752,267, which is a continuation of application No. 11/796,226, filed on Apr. 26, 2007, now abandoned.

(60) Provisional application No. 60/809,088, filed on May 26, 2006.

(51) Int. Cl.

*B29D 23/00* (2006.01)
*A61F 2/82* (2013.01)
*A61F 2/06* (2013.01)
*A61L 31/06* (2006.01)
*A61F 2/915* (2013.01)
*A61L 31/14* (2006.01)
*A61F 2/90* (2013.01)
*A61L 29/00* (2006.01)
*A61F 2/844* (2013.01)
*A61L 31/04* (2006.01)
*B29C 65/48* (2006.01)
*A61F 2/95* (2013.01)
*A61B 90/00* (2016.01)
*B29L 31/00* (2006.01)

(52) U.S. Cl.

CPC .... *Y10T 29/49929* (2015.01); *Y10T 29/49993* (2015.01); *Y10T 156/1034* (2015.01)

(56) References Cited

U.S. PATENT DOCUMENTS 3,687,135 A 8/1972 Stroganov et al.
3,839,743 A 10/1974 Schwarcz
3,900,632 A 8/1975 Robinson
4,104,410 A 8/1978 Malecki
4,110,497 A 8/1978 Hoel
4,321,711 A 3/1982 Mano
4,346,028 A 8/1982 Griffith
4,596,574 A 6/1986 Urist
4,599,085 A 7/1986 Riess et al.
4,612,009 A 9/1986 Drobnik et al.
4,633,873 A 1/1987 Dumican et al.
4,656,083 A 4/1987 Hoffman et al.
4,718,907 A 1/1988 Karwoski et al.
4,722,335 A 2/1988 Vilasi
4,723,549 A 2/1988 Wholey et al.
4,732,152 A 3/1988 Wallstén et al.
4,733,665 A 3/1988 Palmaz
4,739,762 A 4/1988 Palmaz
4,740,207 A 4/1988 Kreamer
4,743,252 A 5/1988 Martin, Jr. et al.
4,768,507 A 9/1988 Fischell et al.
4,776,337 A 10/1988 Palmaz
4,800,882 A 1/1989 Gianturco
4,816,339 A 3/1989 Tu et al.
4,818,559 A 4/1989 Hama et al.
4,850,999 A 7/1989 Planck
4,877,030 A 10/1989 Beck et al.
4,878,906 A 11/1989 Lindemann et al.
4,879,135 A 11/1989 Greco et al.
4,886,062 A 12/1989 Wiktor
4,886,870 A 12/1989 D'Amore et al.
4,902,289 A 2/1990 Yannas
4,977,901 A 12/1990 Ofstead
4,994,298 A 2/1991 Yasuda
5,019,090 A 5/1991 Pinchuk
5,028,597 A 7/1991 Kodama et al.
5,059,211 A 10/1991 Stack et al.
5,061,281 A 10/1991 Mares et al.
5,062,829 A 11/1991 Pryor et al.
5,084,065 A 1/1992 Weldon et al.
5,085,629 A 2/1992 Goldberg et al.
5,100,429 A 3/1992 Sinofsky et al.
5,104,410 A 4/1992 Chowdhary
5,108,417 A 4/1992 Sawyer
5,108,755 A 4/1992 Daniels et al.
5,112,457 A 5/1992 Marchant
5,123,917 A 6/1992 Lee
5,156,623 A 10/1992 Hakamatsuka et al.
5,163,951 A 11/1992 Pinchuk et al.
5,163,952 A 11/1992 Froix
5,163,958 A 11/1992 Pinchuk
5,167,614 A 12/1992 Tessmann et al.
5,192,311 A 3/1993 King et al.
5,197,977 A 3/1993 Hoffman, Jr. et al.
5,234,456 A 8/1993 Silvestrini
5,234,457 A 8/1993 Andersen
5,236,447 A 8/1993 Kubo et al.
5,279,594 A 1/1994 Jackson
5,282,860 A 2/1994 Matsuno et al.
5,289,831 A 3/1994 Bosley
5,290,271 A 3/1994 Jernberg
5,306,286 A 4/1994 Stack et al.
5,306,294 A 4/1994 Winston et al.
5,328,471 A 7/1994 Slepian
5,330,500 A 7/1994 Song
5,342,348 A 8/1994 Kaplan
5,342,395 A 8/1994 Jarrett et al.
5,342,621 A 8/1994 Eury
5,356,433 A 10/1994 Rowland et al.
5,380,976 A 1/1995 Couch
5,383,925 A 1/1995 Schmitt
5,385,580 A 1/1995 Schmitt
5,389,106 A 2/1995 Tower
5,399,666 A 3/1995 Ford
5,423,885 A 6/1995 Williams
5,441,515 A 8/1995 Khosravi et al.
5,443,458 A 8/1995 Eury et al.
5,443,500 A 8/1995 Sigwart
5,455,040 A 10/1995 Marchant
5,464,650 A 11/1995 Berg et al.
5,486,546 A 1/1996 Mathiesen et al.
5,500,013 A 3/1996 Buscemi et al.
5,502,158 A 3/1996 Sinclair et al.
5,507,799 A 4/1996 Sumiya
5,514,379 A 5/1996 Weissleder et al.
5,525,646 A 6/1996 Lundgren et al.
5,527,337 A 6/1996 Stack et al.
5,545,408 A 8/1996 Trigg et al.
5,554,120 A 9/1996 Chen et al.
5,556,413 A 9/1996 Lam
5,565,215 A 10/1996 Gref et al.
5,578,046 A 11/1996 Liu et al.
5,578,073 A 11/1996 Haimovich et al.
5,591,199 A 1/1997 Porter et al.
5,591,607 A 1/1997 Gryaznov et al.
5,593,403 A 1/1997 Buscemi
5,593,434 A 1/1997 Williams
5,599,301 A 2/1997 Jacobs et al.
5,599,922 A 2/1997 Gryaznov et al.
5,603,722 A 2/1997 Phan et al.
5,605,696 A 2/1997 Eury et al.
5,607,442 A 3/1997 Fischell et al.
5,607,467 A 3/1997 Froix
5,618,299 A 4/1997 Khosravi et al.
5,629,077 A 5/1997 Turnlund et al.
5,631,135 A 5/1997 Gryaznov et al.
5,632,771 A 5/1997 Boatman et al.
5,632,840 A 5/1997 Campbell
5,637,113 A 6/1997 Tartaglia et al.
5,649,977 A 7/1997 Campbell
5,656,186 A 8/1997 Mourou et al.
5,667,767 A 9/1997 Greff et al.
5,667,796 A 9/1997 Otten

(56) References Cited

U.S. PATENT DOCUMENTS 5,670,161 A 9/1997 Healy et al.
5,670,558 A 9/1997 Onishi et al.
5,686,540 A 11/1997 Kakizawa
5,693,085 A 12/1997 Buirge et al.
5,700,286 A 12/1997 Tartaglia et al.
5,700,901 A 12/1997 Hurst et al.
5,704,082 A 1/1998 Smith
5,707,385 A 1/1998 Williams
5,711,763 A 1/1998 Nonami et al.
5,716,981 A 2/1998 Hunter et al.
5,725,549 A 3/1998 Lam
5,725,572 A 3/1998 Lam et al.
5,726,297 A 3/1998 Gryaznov et al.
5,728,751 A 3/1998 Patnaik
5,733,326 A 3/1998 Tomonto et al.
5,733,330 A 3/1998 Cox
5,733,564 A 3/1998 Lehtinen
5,733,925 A 3/1998 Kunz et al.
5,741,327 A 4/1998 Frantzen
5,741,881 A 4/1998 Patnaik
5,756,457 A 5/1998 Wang et al.
5,756,476 A 5/1998 Epstein et al.
5,765,682 A 6/1998 Bley et al.
5,766,204 A 6/1998 Porter et al.
5,766,239 A 6/1998 Cox
5,766,710 A 6/1998 Turnlund et al.
5,769,883 A 6/1998 Buscemi et al.
5,770,609 A 6/1998 Grainger et al.
5,780,807 A 7/1998 Saunders
5,800,516 A 9/1998 Fine et al.
5,811,447 A 9/1998 Kunz et al.
5,824,042 A 10/1998 Lombardi et al.
5,824,049 A 10/1998 Ragheb et al.
5,830,178 A 11/1998 Jones et al.
5,830,461 A 11/1998 Billiar
5,830,879 A 11/1998 Isner
5,833,651 A 11/1998 Donovan et al.
5,834,582 A 11/1998 Sinclair et al.
5,836,962 A 11/1998 Gianotti
5,837,313 A 11/1998 Ding et al.
5,837,835 A 11/1998 Gryaznov et al.
5,840,083 A 11/1998 Braach-Maksvytis
5,851,508 A 12/1998 Greff et al.
5,853,408 A 12/1998 Muni
5,854,207 A 12/1998 Lee et al.
5,855,612 A 1/1999 Ohthuki et al.
5,855,618 A 1/1999 Patnaik et al.
5,858,746 A 1/1999 Hubbell et al.
5,865,814 A 2/1999 Tuch
5,868,781 A 2/1999 Killion
5,873,904 A 2/1999 Ragheb et al.
5,874,101 A 2/1999 Zhong et al.
5,874,109 A 2/1999 Ducheyne et al.
5,874,165 A 2/1999 Drumheller
5,876,743 A 3/1999 Ibsen et al.
5,877,263 A 3/1999 Patnaik et al.
5,879,713 A 3/1999 Roth et al.
5,888,533 A 3/1999 Dunn
5,891,192 A 4/1999 Murayama et al.
5,897,955 A 4/1999 Drumheller
5,906,759 A 5/1999 Richter
5,914,182 A 6/1999 Drumheller
5,916,870 A 6/1999 Lee et al.
5,922,005 A 7/1999 Richter et al.
5,942,209 A 8/1999 Leavitt et al.
5,948,428 A 9/1999 Lee et al.
5,954,744 A 9/1999 Phan et al.
5,957,975 A 9/1999 Lafont et al.
5,965,720 A 10/1999 Gryaznov et al.
5,971,954 A 10/1999 Conway et al.
5,976,182 A 11/1999 Cox
5,980,564 A 11/1999 Stinson
5,980,928 A 11/1999 Terry
5,980,972 A 11/1999 Ding
5,981,568 A 11/1999 Kunz et al.
5,986,169 A 11/1999 Gjunter
5,997,468 A 12/1999 Wolff et al.
6,007,845 A 12/1999 Domb et al.
6,010,445 A 1/2000 Armini et al.
6,015,541 A 1/2000 Greff et al.
6,022,374 A 2/2000 Imran
6,042,606 A 3/2000 Frantzen
6,042,875 A 3/2000 Ding et al.
6,048,964 A 4/2000 Lee et al.
6,051,648 A 4/2000 Rhee et al.
6,056,993 A 5/2000 Leidner et al.
6,060,451 A 5/2000 DiMaio et al.
6,066,156 A 5/2000 Yan
6,071,266 A 6/2000 Kelley
6,074,659 A 6/2000 Kunz et al.
6,080,177 A 6/2000 Igaki et al.
6,080,488 A 6/2000 Hostettler et al.
6,083,258 A 7/2000 Yadav
6,093,463 A 7/2000 Thakrar
6,096,070 A 8/2000 Ragheb et al.
6,096,525 A 8/2000 Patnaik
6,099,562 A 8/2000 Ding et al.
6,103,230 A 8/2000 Billiar et al.
6,107,416 A 8/2000 Patnaik et al.
6,110,188 A 8/2000 Narciso, Jr.
6,110,483 A 8/2000 Whitbourne
6,113,629 A 9/2000 Ken
6,117,979 A 9/2000 Hendriks et al.
6,120,536 A 9/2000 Ding et al.
6,120,904 A 9/2000 Hostettler et al.
6,121,027 A 9/2000 Clapper et al.
6,125,523 A 10/2000 Brown et al.
6,127,173 A 10/2000 Eckstein et al.
6,129,761 A 10/2000 Hubbell
6,129,928 A 10/2000 Sarangapani et al.
6,131,266 A 10/2000 Saunders
6,150,630 A 11/2000 Perry et al.
6,153,252 A 11/2000 Hossainy et al.
6,156,062 A 12/2000 McGuinness
6,159,951 A 12/2000 Karpeisky et al.
6,160,084 A 12/2000 Langer et al.
6,160,240 A 12/2000 Momma et al.
6,165,212 A 12/2000 Dereume et al.
6,166,130 A 12/2000 Rhee et al.
6,169,170 B1 1/2001 Gryaznov et al.
6,171,609 B1 1/2001 Kunz
6,174,326 B1 1/2001 Kitaoka et al.
6,174,329 B1 1/2001 Callol et al.
6,174,330 B1 1/2001 Stinson
6,177,523 B1 1/2001 Reich et al.
6,183,505 B1 2/2001 Mohn, Jr. et al.
6,187,045 B1 2/2001 Fehring et al.
6,210,715 B1 4/2001 Starling et al.
6,224,626 B1 5/2001 Steinke
6,228,845 B1 5/2001 Donovan et al.
6,240,616 B1 6/2001 Yan
6,245,076 B1 6/2001 Yan
6,245,103 B1 6/2001 Stinson
6,248,344 B1 6/2001 Ylanen et al.
6,251,135 B1 6/2001 Stinson et al.
6,251,142 B1 6/2001 Bernacca et al.
6,254,632 B1 7/2001 Wu et al.
6,260,976 B1 7/2001 Endou et al.
6,273,913 B1 8/2001 Wright et al.
6,281,262 B1 8/2001 Shikinami
6,283,234 B1 9/2001 Torbet
6,284,333 B1 9/2001 Wang et al.
6,287,332 B1 9/2001 Bolz et al.
6,290,721 B1 9/2001 Heath
6,293,966 B1 9/2001 Frantzen
6,295,168 B1 9/2001 Hoffnagle et al.
6,303,901 B1 10/2001 Perry et al.
6,312,459 B1 11/2001 Huang et al.
6,327,772 B1 12/2001 Zadno-Azizi et al.
6,334,871 B1 1/2002 Dor et al.
6,355,058 B1 3/2002 Pacetti et al.
6,361,557 B1 3/2002 Gittings et al.
6,375,826 B1 4/2002 Wang et al.
6,379,381 B1 4/2002 Hossainy et al.

(56) References Cited

U.S. PATENT DOCUMENTS 6,387,121 B1 5/2002 Alt
6,388,043 B1 5/2002 Langer et al.
6,395,326 B1 5/2002 Castro et al.
6,402,777 B1 6/2002 Globerman et al.
6,409,752 B1 6/2002 Boatman et al.
6,409,761 B1 6/2002 Jang
6,423,092 B2 7/2002 Datta et al.
6,461,632 B1 10/2002 Gogolewski
6,464,720 B2 10/2002 Boatman et al.
6,471,721 B1 10/2002 Dang
6,475,779 B2 11/2002 Mathiowitz et al.
6,479,565 B1 11/2002 Stanley
6,485,512 B1 11/2002 Cheng
6,492,615 B1 12/2002 Flanagan
6,494,908 B1 12/2002 Huxel et al.
6,495,156 B2 12/2002 Wenz et al.
6,506,437 B1 1/2003 Harish et al.
6,511,748 B1 1/2003 Barrows
6,517,888 B1 2/2003 Weber
6,521,865 B1 2/2003 Jones et al.
6,527,801 B1 3/2003 Dutta
6,537,589 B1 3/2003 Chae et al.
6,539,607 B1 4/2003 Fehring et al.
6,540,777 B2 4/2003 Stenzel
6,554,854 B1 4/2003 Flanagan
6,563,080 B2 5/2003 Shapovalov et al.
6,563,998 B1 5/2003 Farah
6,565,599 B1 5/2003 Hong et al.
6,569,191 B1 5/2003 Hogan
6,569,193 B1 5/2003 Cox et al.
6,572,672 B2 6/2003 Yadav et al.
6,574,851 B1 6/2003 Mirizzi
6,582,472 B2 6/2003 Hart
6,585,755 B2 7/2003 Jackson et al.
6,589,227 B2 7/2003 Sønderskov Klint
6,592,614 B2 7/2003 Lenker et al.
6,592,617 B2 7/2003 Thompson
6,613,072 B2 9/2003 Lau et al.
6,620,194 B2 9/2003 Ding et al.
6,626,936 B2 9/2003 Stinson
6,626,939 B1 9/2003 Burnside et al.
6,635,269 B1 10/2003 Jennissen
6,641,607 B1 11/2003 Hossainy et al.
6,645,243 B2 11/2003 Vallana et al.
6,652,579 B1 11/2003 Cox et al.
6,656,162 B2 12/2003 Santini, Jr. et al.
6,664,335 B2 12/2003 Krishnan
6,666,214 B2 12/2003 Canham
6,667,049 B2 12/2003 Janas et al.
6,669,722 B2 12/2003 Chen et al.
6,669,723 B2 12/2003 Killion et al.
6,676,697 B1 1/2004 Richter
6,679,980 B1 1/2004 Andreacchi
6,689,375 B1 2/2004 Wahlig et al.
6,695,920 B1 2/2004 Pacetti et al.
6,696,667 B1 2/2004 Flanagan
6,699,278 B2 3/2004 Fischell et al.
6,706,273 B1 3/2004 Roessler
6,709,379 B1 3/2004 Brandau et al.
6,719,934 B2 4/2004 Stinson
6,719,989 B1 4/2004 Matsushima et al.
6,720,402 B2 4/2004 Langer et al.
6,746,773 B2 6/2004 Llanos et al.
6,752,826 B2 6/2004 Holloway et al.
6,753,007 B2 6/2004 Haggard et al.
6,758,859 B1 7/2004 Dang et al.
6,764,505 B1 7/2004 Hossainy et al.
6,780,261 B2 8/2004 Trozera
6,801,368 B2 10/2004 Coufal et al.
6,805,898 B1 10/2004 Wu et al.
6,818,063 B1 11/2004 Kerrigan
6,822,186 B2 11/2004 Strassl et al.
6,846,323 B2 1/2005 Yip et al.
6,852,946 B2 2/2005 Groen et al.
6,858,680 B2 2/2005 Gunatillake et al.
6,863,685 B2 3/2005 Davila et al.
6,867,389 B2 3/2005 Shapovalov et al.
6,878,758 B2 4/2005 Martin et al.
6,891,126 B2 5/2005 Matile
6,899,729 B1 5/2005 Cox et al.
6,911,041 B1 6/2005 Zscheeg
6,913,762 B2 7/2005 Caplice et al.
6,918,928 B2 7/2005 Wolinsky et al.
6,926,733 B2 8/2005 Stinson
6,943,964 B1 9/2005 Zhang et al.
6,981,982 B2 1/2006 Armstrong et al.
6,981,987 B2 1/2006 Huxel et al.
7,022,132 B2 4/2006 Kocur
7,128,737 B1 10/2006 Goder et al.
7,163,555 B2 1/2007 Dinh
7,166,099 B2 1/2007 Devens, Jr.
7,226,475 B2 6/2007 Lenz et al.
7,243,408 B2 7/2007 Vietmeier
7,326,245 B2 2/2008 Rosenthal et al.
7,331,986 B2 2/2008 Brown et al.
7,500,988 B1 3/2009 Butaric et al.
7,776,926 B1 8/2010 Hossainy et al.
8,752,268 B2 6/2014 Wu
9,038,260 B2 5/2015 Wu
9,358,325 B2 * 6/2016 Wu ........................ B29D 23/00
2001/0001317 A1 5/2001 Duerig et al.
2001/0021871 A1 9/2001 Stinson
2001/0021873 A1 9/2001 Stinson
2001/0027339 A1 10/2001 Boatman et al.
2001/0029398 A1 10/2001 Jadhav
2001/0044652 A1 11/2001 Moore
2002/0002399 A1 1/2002 Huxel et al.
2002/0004060 A1 1/2002 Heublein et al.
2002/0004101 A1 1/2002 Ding et al.
2002/0032486 A1 3/2002 Lazarovitz et al.
2002/0062148 A1 5/2002 Hart
2002/0065553 A1 5/2002 Weber
2002/0103528 A1 8/2002 Schaldach et al.
2002/0111590 A1 8/2002 Davila et al.
2002/0116050 A1 8/2002 Kocur
2002/0138133 A1 9/2002 Lenz et al.
2002/0143386 A1 10/2002 Davila et al.
2002/0161114 A1 10/2002 Gunatillake et al.
2002/0190038 A1 12/2002 Lawson
2002/0193862 A1 12/2002 Mitelberg et al.
2003/0004563 A1 1/2003 Jackson et al.
2003/0028241 A1 2/2003 Stinson
2003/0028245 A1 2/2003 Barclay et al.
2003/0033001 A1 2/2003 Igaki
2003/0039689 A1 2/2003 Chen et al.
2003/0050688 A1 3/2003 Fischell et al.
2003/0060872 A1 3/2003 Gomringer et al.
2003/0065355 A1 4/2003 Weber
2003/0069630 A1 4/2003 Burgermeister et al.
2003/0093107 A1 5/2003 Parsonage et al.
2003/0100865 A1 5/2003 Santini, Jr. et al.
2003/0105518 A1 6/2003 Dutta
2003/0105530 A1 6/2003 Pirhonen
2003/0108588 A1 6/2003 Chen
2003/0121148 A1 7/2003 DiCaprio
2003/0153971 A1 8/2003 Chandrasekaran
2003/0155328 A1 8/2003 Huth
2003/0171053 A1 9/2003 Sanders
2003/0187495 A1 10/2003 Cully et al.
2003/0204245 A1 10/2003 Brightbill
2003/0208259 A1 11/2003 Penhasi
2003/0209835 A1 11/2003 Chun et al.
2003/0226833 A1 12/2003 Shapovalov et al.
2003/0236563 A1 12/2003 Fifer
2004/0015228 A1 1/2004 Lombardi et al.
2004/0024449 A1 2/2004 Boyle
2004/0044399 A1 3/2004 Ventura
2004/0073291 A1 4/2004 Brown et al.
2004/0088039 A1 5/2004 Lee et al.
2004/0093077 A1 5/2004 White et al.
2004/0098090 A1 5/2004 Williams et al.
2004/0098095 A1 5/2004 Burnside et al.
2004/0106987 A1 6/2004 Palasis et al.
2004/0111149 A1 6/2004 Stinson

(56) References Cited

U.S. PATENT DOCUMENTS

| | | | |
|---|---|---|---|
| 2004/0122509 | A1 | 6/2004 | Brodeur |
| 2004/0126405 | A1 | 7/2004 | Sahatjian |
| 2004/0127970 | A1 | 7/2004 | Saunders et al. |
| 2004/0143180 | A1 | 7/2004 | Zhong et al. |
| 2004/0143317 | A1 | 7/2004 | Stinson et al. |
| 2004/0167610 | A1 | 8/2004 | Fleming, III |
| 2004/0167619 | A1 | 8/2004 | Case et al. |
| 2004/0181236 | A1 | 9/2004 | Eidenschink et al. |
| 2004/0204750 | A1 | 10/2004 | Dinh |
| 2004/0220662 | A1 | 11/2004 | Dang et al. |
| 2004/0236428 | A1 | 11/2004 | Burkinshaw et al. |
| 2005/0004653 | A1 | 1/2005 | Gerberding et al. |
| 2005/0004663 | A1 | 1/2005 | Llanos et al. |
| 2005/0015138 | A1 | 1/2005 | Schuessler et al. |
| 2005/0021131 | A1 | 1/2005 | Venkatraman et al. |
| 2005/0060025 | A1 | 3/2005 | Mackiewicz et al. |
| 2005/0087520 | A1 | 4/2005 | Wang et al. |
| 2005/0107865 | A1 | 5/2005 | Clifford et al. |
| 2005/0111500 | A1 | 5/2005 | Harter et al. |
| 2005/0147647 | A1 | 7/2005 | Glauser et al. |
| 2005/0154450 | A1 | 7/2005 | Larson et al. |
| 2005/0157382 | A1 | 7/2005 | Kafka et al. |
| 2005/0172471 | A1 | 8/2005 | Vietmeier |
| 2005/0211680 | A1 | 9/2005 | Li et al. |
| 2005/0222673 | A1 | 10/2005 | Nicholas |
| 2005/0283226 | A1 | 12/2005 | Haverkost |
| 2005/0283228 | A1 | 12/2005 | Stanford |
| 2006/0025847 | A1 | 2/2006 | Parker |
| 2006/0033240 | A1 | 2/2006 | Weber et al. |
| 2006/0120418 | A1 | 6/2006 | Harter et al. |
| 2006/0173528 | A1 | 8/2006 | Feld et al. |
| 2006/0241741 | A1 | 10/2006 | Lootz |
| 2007/0156230 | A1 | 7/2007 | Dugan et al. |
| 2007/0266542 | A1 | 11/2007 | Melsheimer |
| 2007/0293938 | A1 | 12/2007 | Gale et al. |
| 2008/0009938 | A1 | 1/2008 | Huang et al. |
| 2008/0015684 | A1 | 1/2008 | Wu |
| 2008/0033532 | A1 | 2/2008 | Dave |
| 2008/0188924 | A1 | 8/2008 | Prabhu |
| 2009/0076594 | A1 | 3/2009 | Sabaria |
| 2009/0204203 | A1 | 8/2009 | Allen et al. |
| 2010/0004735 | A1 | 1/2010 | Yang et al. |
| 2011/0130521 | A1 | 6/2011 | Thatcher et al. |
| 2011/0282428 | A1 | 11/2011 | Meyer et al. |
| 2013/0150943 | A1 | 6/2013 | Zheng et al. |
| 2013/0325104 | A1 | 12/2013 | Wu |
| 2013/0325105 | A1 | 12/2013 | Wu |
| 2013/0325107 | A1 | 12/2013 | Wu |
| 2013/0331926 | A1 | 12/2013 | Wu |

FOREIGN PATENT DOCUMENTS

| | | |
|---|---|---|
| DE | 197 31 021 | 1/1999 |
| DE | 198 56 983 | 12/1999 |
| DE | 29724852 | 2/2005 |
| DE | 103 61942 | 7/2005 |
| DE | 10 2004 045994 | 3/2006 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0583170 | 2/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0714641 | 6/1996 |
| EP | 0842729 | 5/1998 |
| EP | 0 970 711 | 1/2000 |
| EP | 1210 922 | 6/2002 |
| EP | 1277449 | 1/2003 |
| EP | 1 591 079 | 11/2005 |
| EP | 1 656 905 | 5/2006 |
| GB | 2 247 696 | 3/1992 |
| JP | 4-33791 | 2/1992 |
| JP | 7-124766 | 5/1995 |
| JP | 10-166156 | 6/1998 |
| JP | 2003-53577 | 2/2003 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/27587 | 10/1995 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/20429 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 02/26162 | 4/2002 |
| WO | WO 02/38325 | 5/2002 |
| WO | WO 03/015664 | 2/2003 |
| WO | WO 03/015978 | 2/2003 |
| WO | WO 03/047463 | 6/2003 |
| WO | WO 03/057075 | 7/2003 |
| WO | WO 2004/019820 | 3/2004 |
| WO | WO 2004/023985 | 3/2004 |
| WO | WO 2004/062533 | 7/2004 |
| WO | WO 2004/112863 | 12/2004 |
| WO | WO 2005/023480 | 3/2005 |
| WO | WO 2007/081551 | 7/2007 |
| WO | WO 2009/121048 A1 | 10/2009 |

OTHER PUBLICATIONS

U.S. Appl. No. 11/325,974, Dugan et al., filed Jan. 4, 2006.

U.S. Appl. No. 12/172,020, Wang, filed Jul. 11, 2008.

Acquarulo et al., *Enhancing Medical Device Performance with Nanocomposite Poly*, Med. Device Link, www.devicelink.com/grabber.php3?URL downloaded Mar. 26, 2007, 4 pgs.

Anonymous, *Bioabsorbable stent mounted on a catheter having optical coherence tomography capabilities*, Research Disclosure, Sep. 2004, pp. 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Bull, *Parylene Coating for Medical Applications*, Medical Product Manufacturing News 18, 1 pg. (Mar. 1993).

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

(56) References Cited

OTHER PUBLICATIONS

Devanathan et al., *Polymeric Conformal Coatings for Implantable Electronic Devices*, IEEE Transactions on Biomedical Engineering, vol. BME-27(11), pp. 671-675 (1980).
Eidelman et al., *Characterization of Combinatorial Polymer Blend Composition Gradients by FTIR Microspectroscopy*, J. Res. Natl. Inst. Standards and Technol., vol. 109, No. 2, pp. 219-231 (2004).
Elbert et al., *Conjugate Addition Reactions Combined with Free-Radical Cross-Linking for the Design of Materials for Tissue Engineering*, Biomacromolecules, vol. 2, pp. 430-441 (2001).
Fan et al., *Plasma Absorption of Femtosecond Laser Pulses in Dielectrics*, J. of Heat Transfer, vol. 124, pp. 275-283 (2002).
Feng-Chun et al., *Assessment of Tissue Blood Flow Following Small Artery Welding with an Intraluminal Dissolvable Stent*, Microsurgery, vol. 19(3), pp. 148-152 (1999).
Hahn et al., *Biocompatibility of Glow-Discharge-Polymerized Films and Vacuum-Deposited Parylene*, J Applied Polymer Sci, vol. 38, pp. 55-64 (1984).
Hahn et al., *Glow Discharge Polymers as Coatings for Implanted Devices*, ISA, pp. 109-111 (1981).
He et al., *Assessment of Tissue Blood Flow Following Small Artery Welding with an Intraluminal Dissolvable Stent*, Microsurgery, vol. 19(3), pp. 148-152 (1999).
Hoffnagle et al., *Design and performance of a refractive optical system that converts a Gaussian to a flattop beam*, Applied Optics, vol. 39, No. 30 pp. 5488-5499 (2000).
International Search Rep. for PCT/US2007/015561 filed Jul. 6, 2007, mailed Dec. 4, 2007, 7 pgs.
International Search Report for PCT/US2006/049269, filed Dec. 21, 2006, mailed Jun. 15, 2007, 19 pgs.
Kelley et al., *Totally Resorbable High-Strength Composite Material*, Advances in Biomedical Polymers, vol. 35, pp. 75-85 (1987).
Kubies et al., *Microdomain Structure in polylactide-block-poly(ethylene oxide) copolymer films*, Biomaterials, vol. 21, pp. 529-536 (2000).
Kutryk et al., *Coronary Stenting: Current Perspectives, a companion to the Handbook of Coronary Stents*, pp. 1-16 (1999).
Martin et al., *Enhancing the biological activity of immobilized osteopontin using a type-1 collagen affinity coating*, J. Biomed. Mater. Res., vol. 70A, pp. 10-19 (2004).
Mauduit et al., *Hydrolytic degradation of films prepared from blends of high and low molecular weight poly(DL-lactic acid)s*, J. Biomed. Mater. Res., vol. 30, pp. 201-207 (1996).
Middleton et al., *Synthetic biodegradable polymers as orthopedic devices*, Biomaterials, vol. 21, pp. 2335-2346 (2000).
Muller et al., *Advances in Coronary Angioplasty: Endovascular Stents*, Coron. Arter. Dis., vol. 1(4), pp. 438-448 (Jul./Aug. 1990).
NanoComposix, products, www.nanocomposix.com, dowhloaded Mar. 26, 2007, 2 pgs.
Nanosiliver, Photocatalyst and Nanocomposite Material, http://eng.nanocomposite.net downloaded Mar. 26, 2007, 1 pg.
Nichols et al., *Electrical Insulation of Implantable Devices by Composite Polymer Coatings*, ISA Transactions, vol. 26(4), pp. 15-18 (1987).
Peuster et al., *A novel approach to temporary stenting: degradable cardiovascular stents produced from corrodible metal-results 6-18 months after implantation into New Zealand white rabbits*, Heart, vol. 86, pp. 563-569 (2001).
Pietrzak et al., *Bioabsorbable Fixation Devices: Status for the Craniomaxillofacial Surgeon*, J. Craniofaxial Surg., vol. 2, pp. 92-96 (1997).
Pietrzak et al., *Bioresorbable implants—practical considerations*, Bone, vol. 19, No. 1, Supplement Jul. 1996, pp. 109S-119S.
Redman, *Clinical Experience with Vasovasostomy Utilizing Absorbable Intravasal Stent*, Urology, vol. 20(1), pp. 59-61 (Jul. 1982).
Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).
Schatz, *A View of Vascular Stents*, Circulation, vol. 79(2), pp. 445-457 (Feb. 1989).
Schmidt et al., *Long-Term Implants of Parylene-C Coated Microelectrodes*, Med & Biol Eng & Comp, vol. 26(1), pp. 96-101 (Jan. 1988).
Spagnuolo et al., *Gas 1 is induced by VE-cadherin and vascular endothelial growth factor and inhibits endothelial cell apoptosis*, Blood, vol. 103, pp. 3005-3012 (2004).
Sun et al., "Inert gas beam delivery for ultrafast laser micromachining at ambient pressure", Am. Inst. of Physics, Jun. 15, 2001, 6 pgs.
Tamai et al., *Initial and 6-Month Results of Biodegradable Poly-I-Lactic Acid Coronary Stents in Humans*, Circulation, pp. 399-404 (Jul. 25, 2000).
Tsuji et al., *Biodegradable Polymeric Stents*, Current Interventional Cardiology Reports, vol. 3, pp. 10-17 (2001).
Völkel et al., *Targeting of immunoliposomes to endothelial cells using a single-chain Fv fragment directed against human endoglin (CD105)*, Biochimica et Biophysica Acta 1663, pp. 158-166 (2004).
Von Recum et al., *Degradation of polydispersed poly (L-lactic acid) to modulate lactic acid release*, Biomaterials, vol. 16, pp. 441-445 (1995).
Yau et al., Modern Size-Exclusion Liquid Chromatography, Wiley-Interscience Publication, IX-XV (1979).
Zhang et al., "Single-element laser beam shaper for uniform flat-top profiles" Optics Express, vol. 11, No. 16, pp. 1942-1948 (2003).

* cited by examiner

STENTS WITH RADIOPAQUE MARKERS

CROSS REFERENCE TO RELATED APPLICATION

This application is a continuation of application Ser. No. 14/693,679, filed on Apr. 22, 2015, issued as U.S. Pat. No. 9,358,325. Application Ser. No. 14/693,679 is a continuation of application Ser. No. 14/273,127, filed on May 8, 2014, issued as U.S. Pat. No. 9,038,260. Application Ser. No. 14/273,127 is a continuation of application Ser. No. 13/964,008, filed on Aug. 9, 2013, issued as U.S. Pat. No. 8,752,268, and Ser. No. 13/964,006, filed on Aug. 9, 2013, issued as U.S. Pat. No. 8,752,267. Both of application Ser. Nos. 13/964,008 and 13/964,006 are continuations of application Ser. No. 11/796,226, filed on Apr. 26, 2007, which in turned claims benefit of provisional application No. 60/809,088, filed on May 26, 2006. All of these applications are incorporated herein by reference in their entirety.

BACKGROUND OF THE INVENTION

Field of the Invention

This invention relates to implantable medical devices, such as stents. In particular, the invention relates to polymeric stents with radiopaque markers.

Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The structure of stents is typically composed of scaffolding that includes a pattern or network of interconnecting structural elements or struts. The scaffolding can be formed from wires, tubes, or sheets of material rolled into a cylindrical shape. In addition, a medicated stent may be fabricated by coating the surface of either a metallic or polymeric scaffolding with a polymeric carrier. The polymeric scaffolding may also serve as a carrier of an active agent or drug.

The first step in treatment of a diseased site with a stent is locating a region that may require treatment such as a suspected lesion in a vessel, typically by obtaining an x-ray image of the vessel. To obtain an image, a contrast agent, which contains a radiopaque substance such as iodine is injected into a vessel. "Radiopaque" refers to the ability of a substance to absorb x-rays. The x-ray image depicts the lumen of the vessel from which a physician can identify a potential treatment region. The treatment then involves both delivery and deployment of the stent. "Delivery" refers to introducing and transporting the stent through a bodily lumen to a region in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

The stent must be able to simultaneously satisfy a number of mechanical requirements. First, the stent must be capable of withstanding the structural loads, namely radial compressive forces, imposed on the stent as it supports the walls of a vessel lumen. In addition to having adequate radial strength or more accurately, hoop strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion, which typically requires substantial deformation of localized portions of the stent's structure. Once expanded, the stent must maintain its size and shape throughout its service life despite the various forces that may come to bear thereon, including the cyclic loading induced by the beating heart. Finally, the stent must be biocompatible so as not to trigger any adverse vascular responses.

In addition to meeting the mechanical requirements described above, it is desirable for a stent to be radiopaque, or fluoroscopically visible under x-rays. Accurate stent placement is facilitated by real time visualization of the delivery of a stent. A cardiologist or interventional radiologist can track the delivery catheter through the patient's vasculature and precisely place the stent at the site of a lesion. This is typically accomplished by fluoroscopy or similar x-ray visualization procedures. For a stent to be fluoroscopically visible it must be more absorptive of x-rays than the surrounding tissue. Radiopaque materials in a stent may allow for its direct visualization.

In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials may be configured to meet this additional clinical requirement since they may be designed to completely erode after the clinical need for them has ended. Stents fabricated from biodegradable polymers are particularly promising, in part because they may be designed to completely erode within a desired time frame.

However, a significant shortcoming of biodegradable polymers (and polymers generally composed of carbon, hydrogen, oxygen, and nitrogen) is that they are radiolucent with no radiopacity. Biodegradable polymers tend to have x-ray absorption similar to body tissue.

One way of addressing this problem is to attach or couple radiopaque markers to a stent. The radiopaque markers allow the position of the stent to be monitored since the markers are can be imaged by X-ray imaging techniques. The ability to monitor or detect a stent visually is limited by the visibility of the markers.

SUMMARY OF THE INVENTION

Various embodiments of the present invention include a stent comprising radiopaque markers disposed on or within the stent, wherein the radiopaque markers are arranged longitudinally along an axis of the stent.

Further embodiments of the present invention include a stent comprising radiopaque markers disposed on or within the stent, wherein the radiopaque markers are arranged in a pattern along the circumference of the stent.

Additional embodiments of the present invention include a stent comprising a plurality of radiopaque markers disposed on or within on the stent, wherein the plurality of radiopaque markers are selectively arranged in a region of the stent to enhance the visibility of the stent with an imaging technique.

DETAILED DESCRIPTION OF THE INVENTION

The present invention may be applied to stents and, more generally, implantable medical devices such as, but not limited to, self-expandable stents, balloon-expandable stents, stent-grafts, vascular grafts, cerebrospinal fluid shunts, pacemaker leads, closure devices for patent foramen ovale, and synthetic heart valves.

A stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. The present invention is applicable to virtually any stent design and is, therefore, not limited to any particular stent design or pattern. One embodiment of a stent pattern may include cylindrical rings composed of struts. The cylindrical rings may be connected by connecting struts.

In some embodiments, a stent of the present invention may be formed from a tube by laser cutting the pattern of struts in the tube. The stent may also be formed by laser cutting a polymeric sheet, rolling the pattern into the shape of the cylindrical stent, and providing a longitudinal weld to form the stent. Other methods of forming stents are well known and include chemically etching a polymeric sheet and rolling and then welding it to form the stent. A polymeric wire may also be coiled to form the stent. The stent may be formed by injection molding of a thermoplastic or reaction injection molding of a thermoset polymeric material. Filaments of the compounded polymer may be extruded or melt spun. These filaments can then be cut, formed into ring elements, welded closed, corrugated to form crowns, and then the crowns welded together by heat or solvent to form the stent. Lastly, hoops or rings may be cut from tubing stock, the tube elements stamped to form crowns, and the crowns connected by welding or laser fusion to form the stent.

Figure 1:
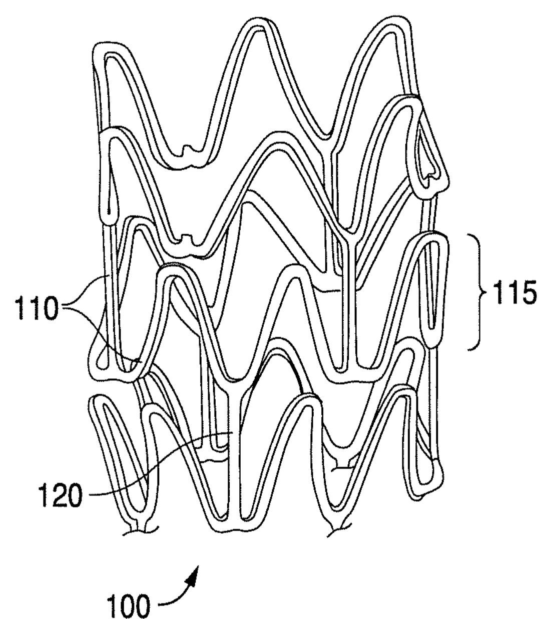
FIG. 1 depicts an exemplary stent.

FIG. 1 depicts an exemplary stent 100 with struts 110 that form cylindrical rings 115 which are connected by linking struts 120. The cross-section of the struts in stent 100 are rectangular-shaped. The cross-section of struts is not limited to what has been illustrated, and therefore, other cross-sectional shapes are applicable with embodiments of the present invention. The pattern should not be limited to what has been illustrated as other stent patterns are easily applicable with embodiments of the present invention.

A stent can be made of a biostable and/or biodegradable polymer. As indicated above, a stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind. The duration can be in a range from about a month to a few years. However, the duration is typically in a range from about one month to twelve months, or in some embodiments, six to twelve months. It is important for the stent to provide mechanical support to a vessel for at least a portion of the duration. Many biodegradable polymers have erosion rates that make them suitable for treatments that require the presence of a device in a vessel for the above-mentioned time-frames.

As indicated above, it is desirable to have the capability of obtaining images of polymeric stents with x-ray fluoroscopy during and after implantation. Various embodiments of the present invention include stents with markers arranged in patterns or selectively arranged on the stent in a manner that facilitates visualization of the stent.

Various types of markers can be used in embodiments of the present invention. Representative types of markers include constructs made of a radiopaque material that is disposed within depots or holes in a stent. The construct can be, but is not limited to a pellet, bead, or slug. The depot or hole can be made to accommodate the shape of the marker. In an embodiment, the depot may be formed in a structural element by laser machining. The depot may extend partially or completely through the portion of the stent. For example, an opening of a depot may be on an abluminal or luminal surface and extend partially through the stent or completely through to an opposing surface. The markers may be sufficiently radiopaque for imaging the stent. In addition, embodiments of the stents with markers should be biocompatible and should not interfere with treatment.

Figure 2:
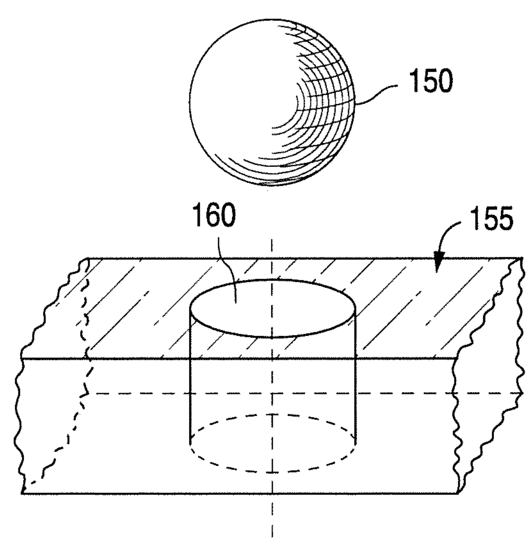
FIG. 2 depicts an exemplary embodiment of a radiopaque marker and a section of a structural element of a stent with a depot for receiving the marker.

FIG. 2 illustrates an exemplary embodiment of a spherical marker 150 and a section 155 of a structural element of a stent with a cylindrical depot 160. Depot 160 accommodates the shape of spherical marker 150 so that is can be positioned within depot 160. Markers can be attached or coupled to a stent using various techniques, including, but not limited to, gluing, welding, or through an interference fit.

The markers and manner of positioning on the stent are merely representative. Embodiments of the present invention are not limited to the type of marker or the manner of attachment or coupling to the stent. The present invention applies to markers that can be attached or coupled in, on, or around a stent at a specific locations or positions on the stent structure or geometry.

In general, increasing the size of a marker enhances the visibility of a stent. However, increasing the size of a marker can have disadvantages. For example, a larger marker can result in an undesirably large profile of the stent which can interfere with the flow of blood in a vessel. Complications such as thrombosis can result from the disturbed blood flow. Additionally, a larger marker disposed in a structural element can negatively affect its structural integrity.

Embodiments of the present invention are directed to positioning or arranging markers on a stent to facilitate detection or monitoring the position of the stent. In certain embodiments, the markers can be arranged in a geometrical pattern that facilitates visualization of the stent.

Figure 3:
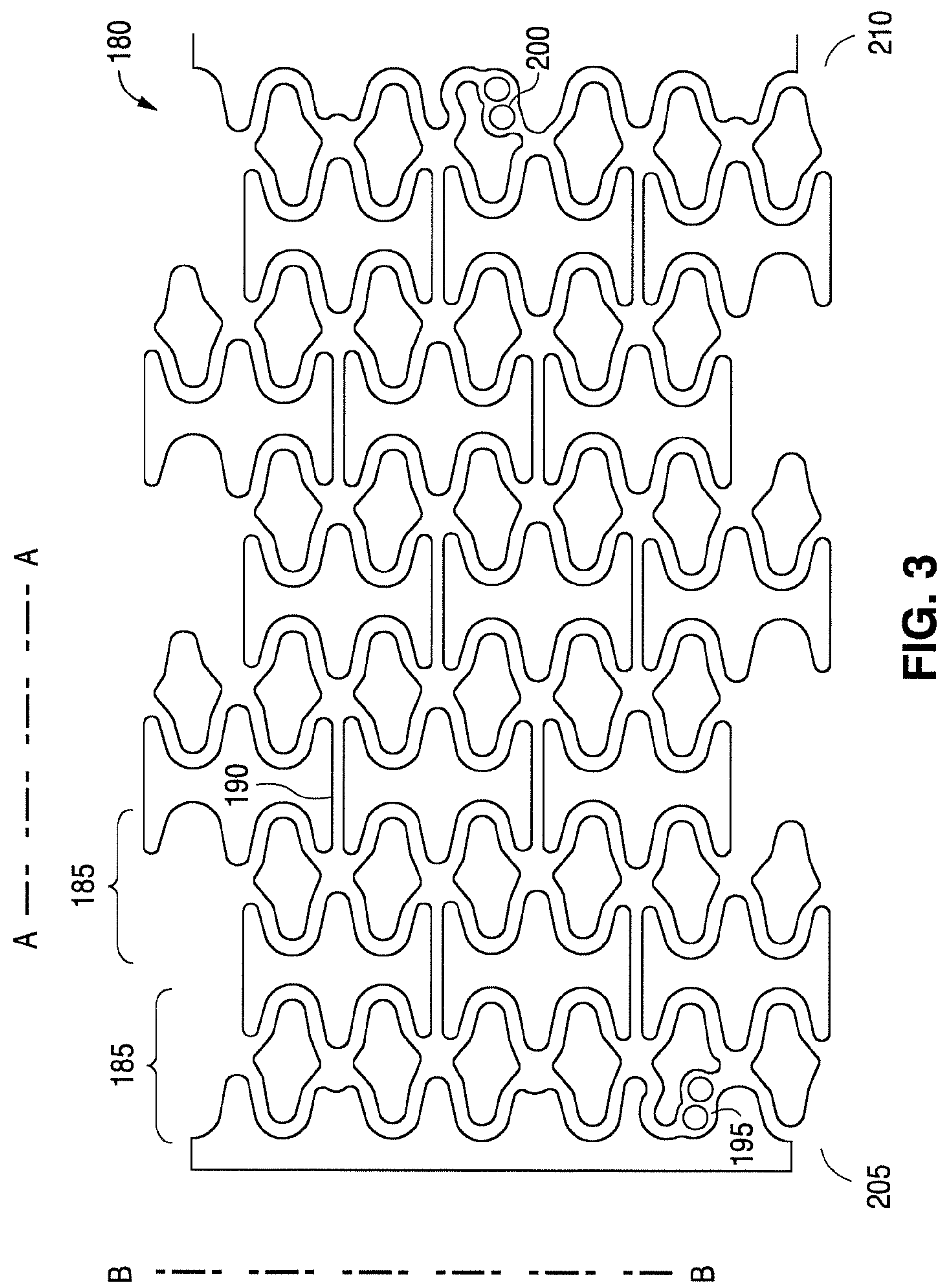
FIG. 3 depicts a stent pattern with radiopaque markers at proximal and distal ends.

FIG. 3 depicts a stent pattern 180 in a flattened condition showing an abluminal or luminal surface so that the pattern can be clearly viewed. When the flattened portion of stent pattern 180 is in a cylindrical condition, it forms a radially expandable stent. Line A-A corresponds to the longitudinal axis of a stent made from stent pattern 180 and line B-B corresponds to the circumferential direction of a stent made from stent pattern 180.

Stent pattern 180 includes cylindrically aligned rings 185 and linking structural elements 190. Structural elements at a proximal end 205 and distal end 210 of stent pattern 180 include depots with pairs of radiopaque markers 195 and 200, respectively, disposed within the depots. As shown FIG. 3, the structural elements are thicker in the vicinity of markers 195 and 200 to compensate for the presence of the depots. In general, it is desirable to place radiopaque markers in regions of a stent pattern that experience relatively low strain during crimping and expansion. Such low strain regions include straight portions of structural elements and "spider regions" which are intersections of three or more structural elements.

A physician can monitor the position of the stent due to the presence of the radiopaque markers which are visible using X-ray imaging. Since markers are located at the distal and proximal ends of the stent, the positions of the markers allow the physician to locate the ends of the stent. However, the small size of the markers can make it difficult to visually detect the individual markers. As indicated above, the size of markers is limited by a desired profile of the stent and structural integrity of structural elements. Since the markers are separated by the length of the stent, locating the ends of the stent can be difficult.

Various embodiments of the present invention include a stent having radiopaque markers arranged in patterns or selectively arranged in a region in a manner that enhances or facilitates visualization of the stent. Radiopaque markers arranged in patterns or selectively arranged in particular region(s) have greater visibility than one or two localized markers and can substantially enhance the visibility of a stent.

Figure 4:
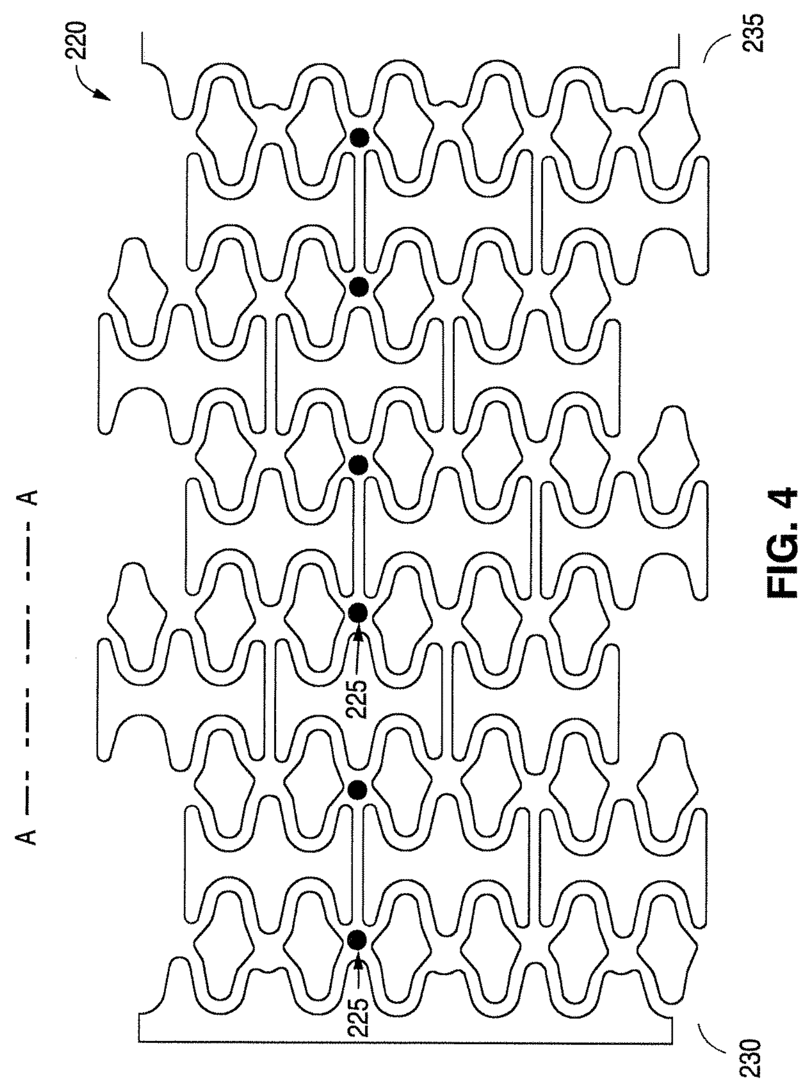
FIG. 4 depicts a stent pattern with radiopaque markers arranged longitudinally along the cylindrical axis.

FIG. 4 depicts an exemplary stent pattern 220 of the present invention. Stent pattern 220 is the same as pattern 180 in FIG. 3 except for the number and arrangement of radiopaque markers. Stent pattern 220 includes radiopaque markers 225 which are arranged longitudinally along the cylindrical axis of stent pattern 220. Radiopaque markers 225 can be placed in or on any portion of the structural elements of stent pattern 220, as long as the mechanical integrity of the structural element is not undesirably compromised. As shown in FIG. 4, radiopaque markers 220 are located in the "spider regions," which are relatively low strain regions of stent pattern 220. Such a pattern is substantially more visible than one or two markers localized at either end of the stent, as depicted in FIG. 3.

The longitudinal pattern of markers 225 extends from a proximal end 230 to a distal end 235 of stent pattern 220. In some embodiments, the pattern does not extend all the way between the proximal end and distal end. A portion between the proximal and distal ends can be devoid of markers.

Figure 5:
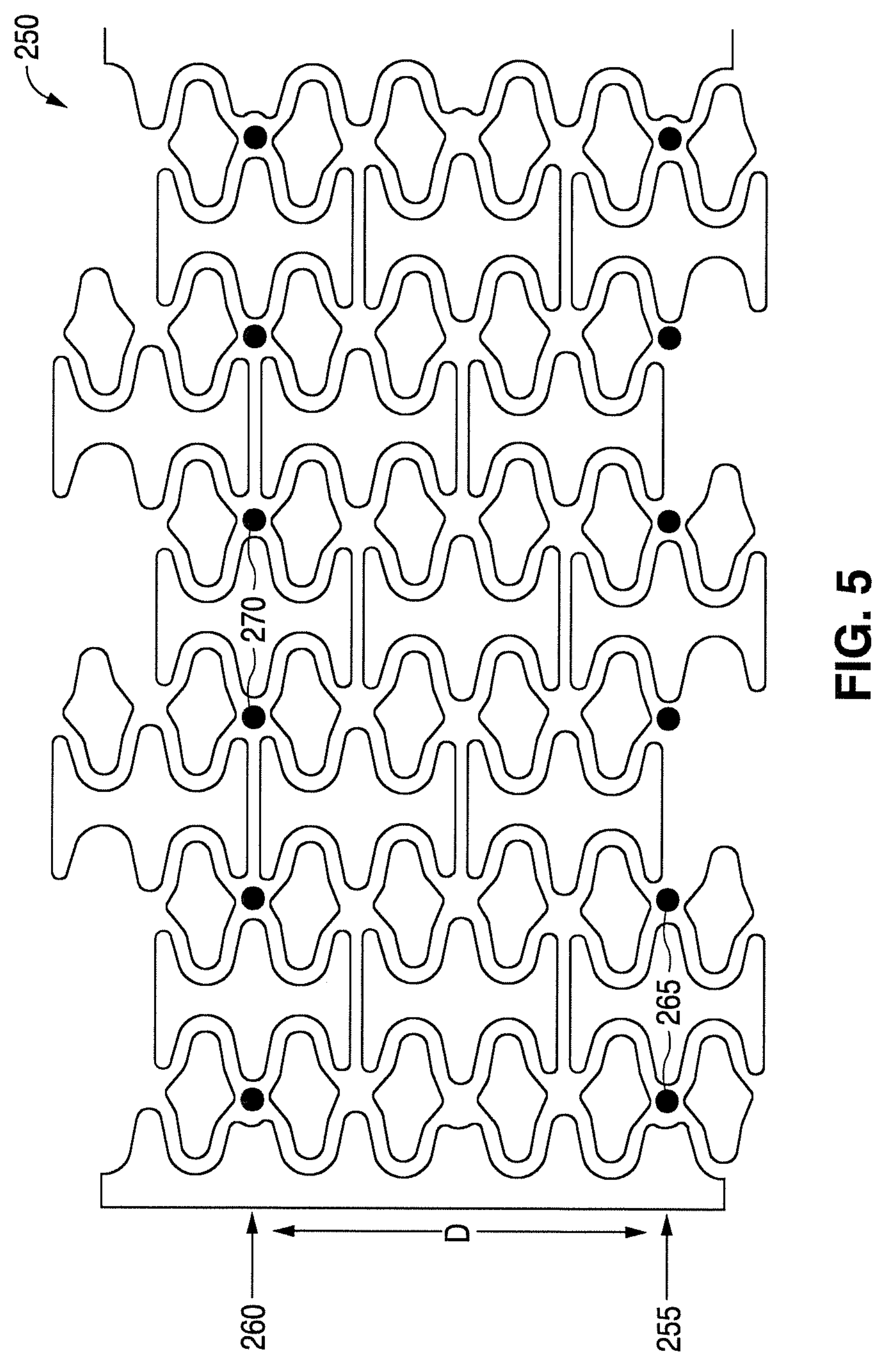
FIG. 5 depicts a stent pattern with radiopaque markers arranged in two longitudinally patterns along the cylindrical axis.

In other embodiments, the visibility of the stent can be further enhanced by including additional marker patterns. For example, FIG. 5 depicts another exemplary stent pattern 250 of the present invention that is the same as the stent patterns of FIGS. 3 and 4 except for the number and arrangement of radiopaque markers. Stent pattern 250 includes a longitudinal pattern 255 of markers 265 and another longitudinal pattern 260 of markers 270 at a different circumferential position. Marker patterns 255 and 260 are separated by a circumferential distance or arc D. D can be between 0° and 45°, 45° and 90°, 90° and 135°, and between 135 and 180°.

Figure 6:
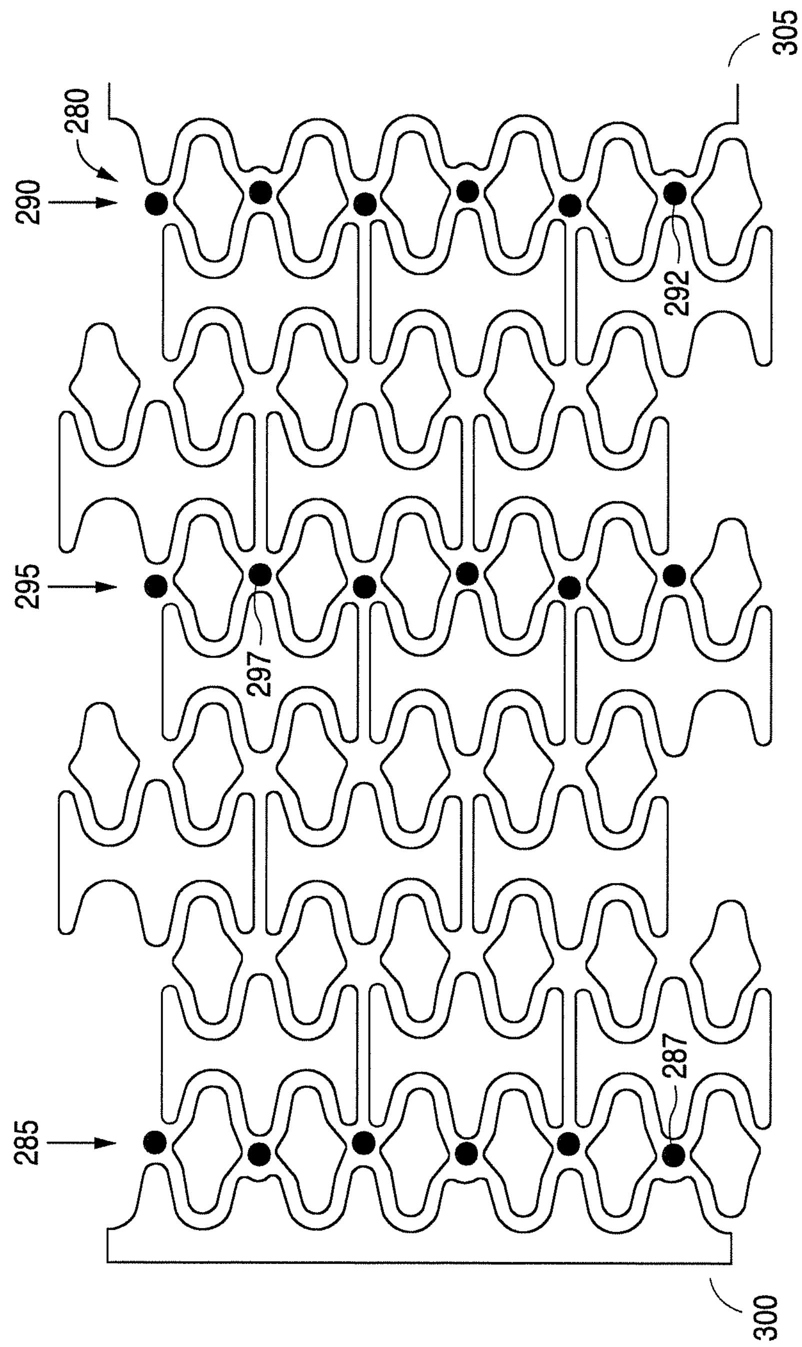
FIG. 6 depicts a stent pattern with radiopaque markers arranged in circumferential patterns.

Further embodiments can include marker patterns along at least a portion of the circumference. Such marker patterns can include, but are not limited to, a circular pattern, diagonal pattern, or a spiral pattern. FIG. 6 depicts another exemplary stent pattern 280 of the present invention that is the same as the previous stent patterns except for the number and arrangement of radiopaque markers. Stent pattern 280 includes three circumferential marker patterns: a marker pattern 285 with markers 287 at a proximal end 300, a marker pattern 290 with markers 292 at a distal end 305, and a marker pattern 295 with markers 297 between proximal end 300 and distal end 305. These marker patterns substantially enhance the visibility of the ends of the stent as compared to one or two markers at the ends, such as that illustrated in FIG. 3.

Figure 7:
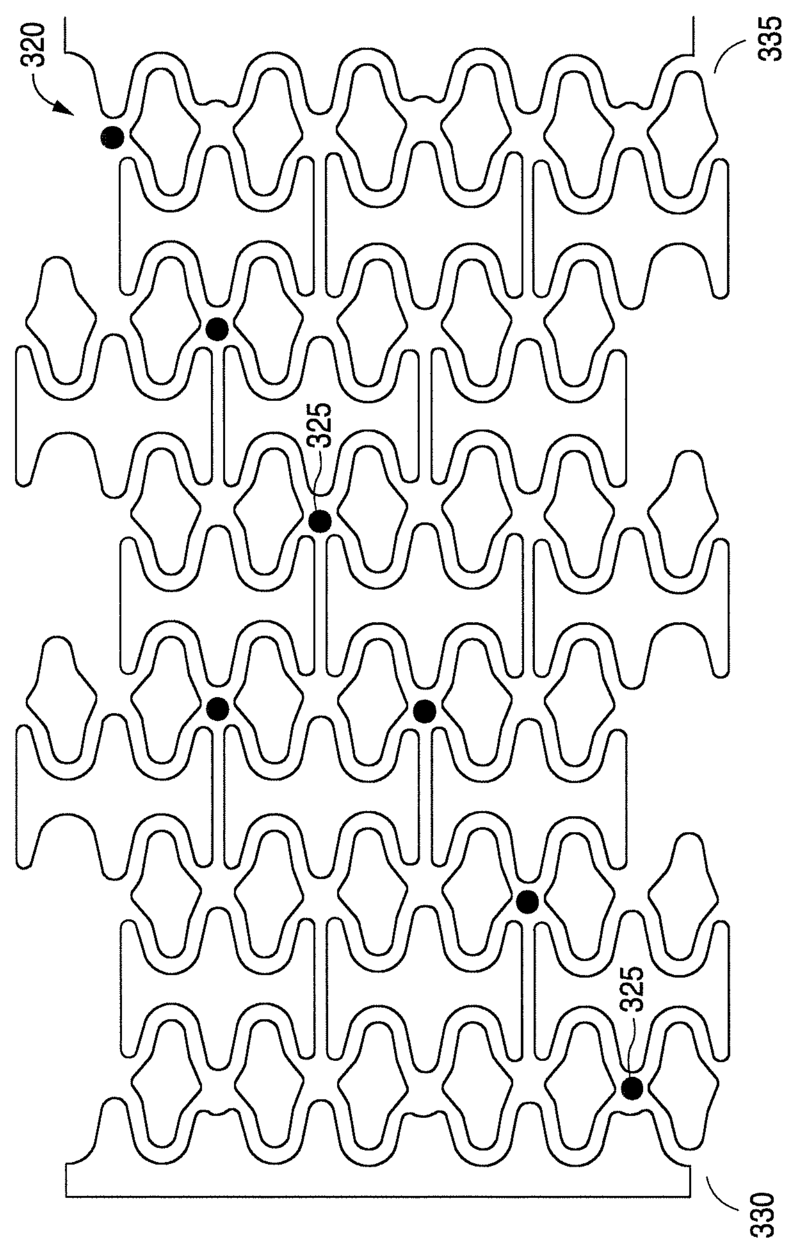
FIG. 7 depicts a stent pattern with radiopaque markers arranged in a diagonal pattern.

Each of the circumferential patterns extends all the way around the circumference of a stent made from stent pattern 280 and is positioned at a single axial position. Alternatively, the circumferential patterns can extend partially around the circumference. Circumferential patterns can also extend diagonally around the circumference so that the marker pattern is not a single axial position. For example, FIG. 7 depicts an exemplary stent pattern 320 that has a diagonal marker pattern with markers 325 extending between a proximal end 330 to a distal end 335.

Figure 8:
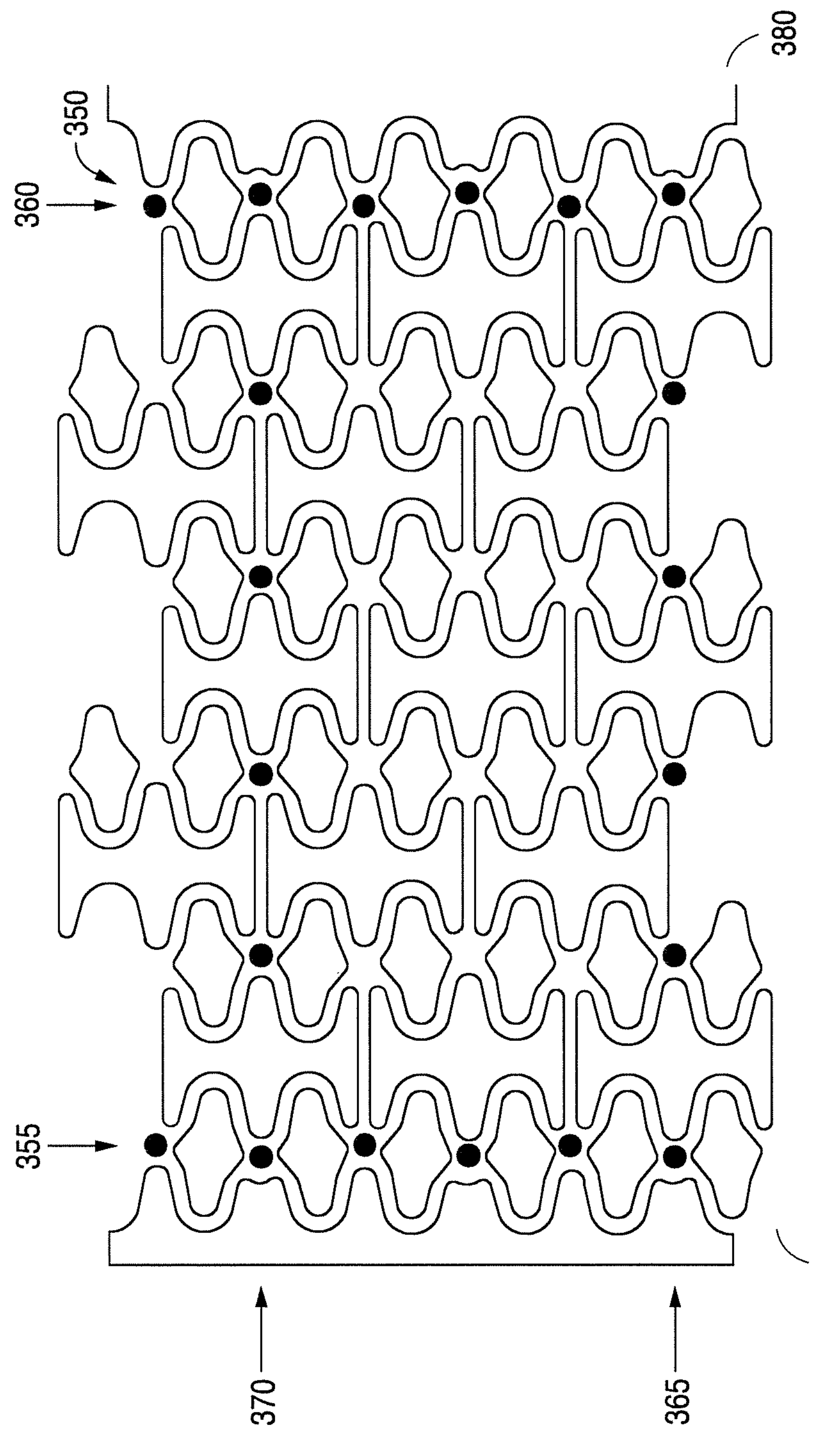
FIG. 8 depicts a stent pattern with radiopaque markers arranged in circumferential patterns and longitudinal patterns.

In some embodiments, a stent can include both longitudinal and circumferential marker patters. FIG. 8 depicts an exemplary stent pattern 350 of the present invention that is the same as the previous stent patterns except for the number and arrangement of radiopaque markers. Stent pattern 350 includes two circumferential marker patterns, 355 and 360, and two longitudinal marker patterns, 365 and 370. Marker patterns 355 and 360 are at proximal end 375 and 380. Such a combination of patterns enhances the visibility of both the ends of the stent as well as the longitudinal extent of the stent.

Figure 9:
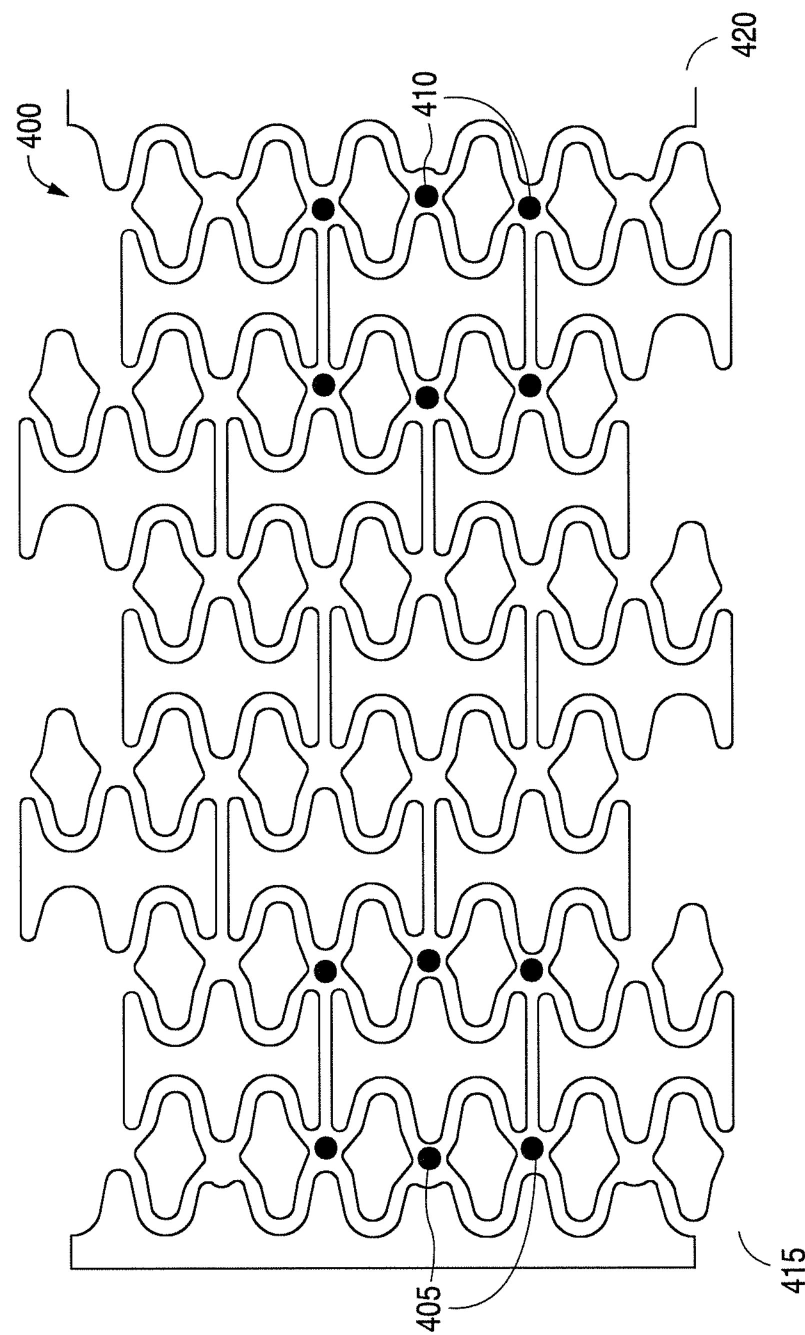
FIG. 9 depicts a stent pattern with radiopaque markers selectively arranged in the proximal and distal regions of a stent.

In certain embodiments, a plurality of radiopaque markers can be selectively arranged in a region of the stent to enhance the visibility of the stent with an imaging technique. For example, the markers can be selectively arranged at a proximal region, distal region, or both. FIG. 9 depicts an exemplary stent pattern 400 of the present invention that is the same as the previous stent patterns except for the number and arrangement of radiopaque markers. Stent pattern 400 includes a group of markers 405 arranged at a proximal end 415 and a group of markers 410 arranged at a distal end 420. The groups of markers tend to increase the visibility of the respective ends of the stent as compared to the markers is FIG. 3. The individual markers can be selected and coupled in a way that there is little or no negative effect on the structural integrity of the stent and also with a relatively low profile.

As indicated above, a stent may have regions with a lower strain than other higher strain regions when the stent is placed under an applied stress during use. A depot for a radiopaque marker may be selectively positioned in a region of lower strain. The selected region of the structural element may be modified to have a higher mass or thickness than a region of lower strain without a marker so as to maintain the load-bearing capability of the region and to inhibit decoupling of the marker from the stent.

Furthermore, the markers may be coupled to any desired location on a stent. In some embodiments, it may be advantageous to limit the placement of a marker to particular locations or portions of surfaces of a stent. For example, it may be desirable to couple a marker at a sidewall face of a structural element to reduce or eliminate interference with a lumen wall or interference with blood flow, respectively. To delineate just the margins of the stent so that the physician may see its full length, markers can be placed only at the distal and proximal ends of the stent.

As indicated above, a stent may include a biostable and/or a biodegradable polymer. The biodegradable polymer may be a pure or substantially pure biodegradable polymer. Alternatively, the biodegradable polymer may be a mixture of at least two types of biodegradable polymers. The stent may be configured to completely erode away once its function is fulfilled.

In certain embodiments, the marker may be biodegradable. It may be desirable for the marker to degrade at the same or substantially the same rate as the stent. For instance, the marker may be configured to completely or almost completely erode at the same time or approximately the same time as the stent. In other embodiments, the marker may degrade at a faster rate than the stent. In this case, the marker may completely or almost completely erode before the body of the stent is completely eroded.

Furthermore, a radiopaque marker may be composed of a biodegradable and/or biostable metal. Biodegradable or bioerodable metals tend to erode or corrode relatively rapidly when exposed to bodily fluids. Biostable metals refer to metals that are not biodegradable or bioerodable or have negligible erosion or corrosion rates when exposed to bodily fluids. Additionally, it is desirable to use a biocompatible biodegradable metal for a marker. A biocompatible biodegradable metal forms erosion products that do not negatively impact bodily functions.

In one embodiment, a radiopaque marker may be composed of a pure or substantially pure biodegradable metal. Alternatively, the marker may be a mixture or alloy of at least two types of metals. Representative examples of biodegradable metals for use in a marker may include, but are not limited to, magnesium, zinc, tungsten, and iron. Representative mixtures or alloys may include magnesium/zinc, magnesium/iron, zinc/iron, and magnesium/zinc/iron. Radiopaque compounds such as iodine salts, bismuth salts, or barium salts may be compounded into the metallic biodegradable marker to further enhance the radiopacity. Representative examples of biostable metals can include, but are not limited to, platinum and gold.

In some embodiments, the composition of the marker may be modified or tuned to obtain a desired erosion rate and/or degree of radiopacity. For example, the erosion rate of the marker may be increased by increasing the fraction of a faster eroding component in an alloy. Similarly, the degree of radiopacity may be increased by increasing the fraction of a more radiopaque metal, such as iron, in an alloy. In one embodiment, a biodegradable marker may be completely eroded when exposed to bodily fluids, such as blood, between about a week and about three months, or more narrowly, between about one month and about two months.

In other embodiments, a radiopaque marker may be a mixture of a biodegradable polymer and a radiopaque material. A radiopaque material may be biodegradable and/or bioabsorbable. Representative radiopaque materials may include, but are not limited to, biodegradable metallic particles and particles of biodegradable metallic compounds such as biodegradable metallic oxides, biocompatible metallic salts, gadolinium salts, and iodinated contrast agents.

In some embodiments, the radiopacity of the marker may be increased by increasing the composition of the radiopaque material in the marker. In one embodiment, the radiopaque material may be between 10% and 80%; 20% and 70%; 30% and 60%; or 40% and 50% by volume of the marker.

The biodegradable polymer in the marker may be a pure or substantially pure biodegradable polymer. Alternatively, the biodegradable polymer may be a mixture of at least two types of biodegradable polymers. In one embodiment, the composition of the biodegradable polymer may be modified to alter the erosion rate of the marker since different biodegradable polymers have different erosion rates.

A biocompatible metallic salt refers to a salt that may be safely absorbed by a body. Representative biocompatible metallic salts that may used in a marker include, but are not limited to, ferrous sulfate, ferrous gluconate, ferrous carbonate, ferrous chloride, ferrous fumarate, ferrous iodide, ferrous lactate, ferrous succinate, barium sulfate, bismuth subcarbonate, bismuth potassium tartrate, bismuth sodium iodide, bismuth sodium tartrate, bismuth sodium triglycollamate, bismuth subsalicylate, zinc acetate, zinc carbonate, zinc citrate, zinc iodate, zinc iodide, zinc lactate, zinc phosphate, zinc salicylate, zinc stearate, zinc sulfate, and combinations thereof. The concentration of the metallic salt in the marker may be between 10% and 80%; 20% and 70%; 30% and 60%; or 40% and 50% by volume of the marker.

In addition, representative iodinated contrast agents may include, but are not limited to acetriozate, diatriozate, iodimide, ioglicate, iothalamate, ioxithalamate, selectan, uroselectan, diodone, metrizoate, metrizamide, iohexol, ioxaglate, iodixanol, lipidial, ethiodol, and combinations thereof. The concentration of an iodinated contrast agent in the marker may be between 5% and 80%; 20% and 70%; 30% and 60%; or 40% and 50% by volume of the marker.

The composition of metallic particles may include at least those biodegradable metals discussed above as well as metallic compounds such as oxides. The concentration of metallic particles in the marker may be between 10% and 80%; 20% and 70%; 30% and 60%; or 40% and 50% by volume of the marker. Additionally, individual metallic particles may be a pure or substantially pure metal or a metal compound. Alternatively, individual metallic particles may be a mixture of at least two types of metals or metallic compounds. Individual metallic particles may also be a mixture or an alloy composed of at least two types of metals.

In certain embodiments, the metallic particles may be metallic nanoparticles. A "nanoparticle" refers to a particle with a dimension in the range of about 1 nm to about 100 nm. A significant advantage of nanoparticles over larger particles is that nanoparticles may disperse more uniformly in a polymeric matrix, which results in more uniform properties such as radiopacity and erosion rate. Additionally, nanoparticles may be more easily absorbed by bodily fluids such as blood without negative impact to bodily functions. Representative examples of metallic particles may include, but are not limited to, iron, magnesium, zinc, platinum, gold, tungsten, and oxides of such metals.

In one embodiment, the composition of different types of metallic particles in the mixture as well as the composition of individual particles may be modified to alter erosion rates and/or radiopacity of the marker. In addition, the ratio of polymer to metallic particles may be modified to alter both the erosion rate, and radiopacity.

A marker may be fabricated by methods including, but not limited to, molding, machining, assembly, or a combination thereof. All or part of a metallic or polymeric marker may be fabricated in a mold or machined by a method such as laser machining.

In general, polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed and/or eliminated by the body.

Biodegradation refers generally to changes in physical and chemical properties that occur in a polymer upon exposure to bodily fluids as in a vascular environment. The changes in properties may include a decrease in molecular weight, deterioration of mechanical properties, and decrease in mass due to erosion or absorption. Mechanical properties may correspond to strength and modulus of the polymer. Deterioration of the mechanical properties of the polymer decreases the ability of a stent, for example, to provide mechanical support in a vessel. The decrease in molecular weight may be caused by, for example, hydrolysis, oxidation, enzymolysis, and/or metabolic processes.

Representative examples of polymers that may be used to fabricate embodiments of stents, or more generally, implantable medical devices include, but are not limited to, poly (N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly (trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of crimping a stent on a balloon, comprising:

(a) providing a biodegradable polymeric stent, wherein structural elements of the stent are made from a polymer;

wherein the polymeric stent includes markers to provide capability of obtaining images of the markers with an imaging device during and after implantation of the stent in a vessel, wherein the stent has first and second markers being attached in an adjacent configuration about a proximal region of the stent, and third and fourth markers being attached in an adjacent configuration about a distal region of the stent, such that the stent has no other markers but for the four markers to allow for imaging of the markers and such that an entire length of the stent between the first pair and second pair of markers is devoid of any markers, wherein the first marker is positioned at a circumferential distance from its adjacent second marker, wherein the third marker is positioned at a circumferential distance from its adjacent fourth marker, and wherein the pair of markers about the proximal region of the polymeric stent are circumferentially off-set from the pair of markers about the distal region of the polymeric stent; and (b) crimping the stent on a balloon of a catheter assembly by application of a crimping pressure to the stent positioned over the balloon, wherein the four markers are deposited in cylindrical depots, wherein the four markers are a mixture or alloy of two types of metals, and wherein the four markers deposited in the cylindrical depots include a gluing material.

2. A method of crimping a stent on a balloon, comprising:

(a) providing a biodegradable polymeric stent, wherein the polymeric stent includes markers to provide capability of obtaining images of the markers with an imaging device during and after implantation of the stent in a vessel, wherein the stent has first and second markers being attached in an adjacent configuration about a proximal region of the stent, and third and fourth markers being attached in an adjacent configuration about a distal region of the stent, such that the stent has no other markers but for the four markers to allow for imaging of the markers and such that an entire length of the stent between the first pair and second pair of markers is devoid of any markers, wherein the first marker is positioned at a circumferential distance from its adjacent second marker, wherein the third marker is positioned at a circumferential distance from its adjacent fourth marker, and wherein the pair of markers about the proximal region of the polymeric stent are circumferentially off-set from the pair of markers about the distal region of the polymeric stent; and (b) crimping the stent on a balloon of a catheter assembly by application of a crimping pressure to the stent positioned over the balloon, wherein the markers are configured off of sidewalls of structural elements, wherein the four markers are deposited in cylindrical depots, wherein the four markers are a mixture or alloy of two types of metals, and wherein a gluing material is deposited in the cylindrical depots for holding the four markers.

* * * * *